United States Patent
Iwano et al.

(10) Patent No.: US 9,867,946 B2
(45) Date of Patent: Jan. 16, 2018

(54) GASKET FOR PRE-FILLED SYRINGE

(71) Applicant: SUMITOMO RUBBER INDUSTRIES, LTD., Kobe-shi, Hyogo (JP)

(72) Inventors: Shinya Iwano, Kobe (JP); Katsushi Maeda, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 81 days.

(21) Appl. No.: 14/194,888

(22) Filed: Mar. 3, 2014

(65) Prior Publication Data
US 2014/0288508 A1 Sep. 25, 2014

(30) Foreign Application Priority Data
Mar. 21, 2013 (JP) .................. 2013-058466

(51) Int. Cl.
A61M 5/315 (2006.01)
A61L 31/08 (2006.01)
A61L 31/10 (2006.01)

(52) U.S. Cl.
CPC ....... A61M 5/31513 (2013.01); A61L 31/084 (2013.01); A61L 31/10 (2013.01); A61M 2205/0222 (2013.01); A61M 2205/0238 (2013.01); A61M 2207/10 (2013.01)

(58) Field of Classification Search
CPC .......... A61L 31/084; A61L 31/10; A61M 2205/0222; A61M 2205/0238; A61M 2207/10; A61M 5/31513
See application file for complete search history.

(56) References Cited

U.S. PATENT DOCUMENTS

| 4,303,070 A | 12/1981 | Ichikawa et al. |
| 7,766,882 B2* | 8/2010 | Sudo ................. A61M 5/31511 604/218 |
| 2013/0053786 A1* | 2/2013 | Maeda .................... B29C 33/42 604/187 |
| 2014/0062036 A1* | 3/2014 | Maeda ............... A61M 5/31511 277/615 |
| 2014/0207075 A1* | 7/2014 | Yotsutsuji ..................... 604/192 |

FOREIGN PATENT DOCUMENTS

| JP | 57-22766 A | 2/1982 |
| JP | 6-343677 A | 12/1994 |
| JP | 2003-199824 A | 7/2003 |
| JP | 2006-181027 A | 7/2006 |

* cited by examiner

Primary Examiner — Imani Hayman
(74) Attorney, Agent, or Firm — Birch, Stewart, Kolasch & Birch, LLP

(57) ABSTRACT

The present invention aims to provide a pre-filled syringe coated with a resin film capable of reducing sliding resistance and preventing liquid leakage by a simple method. The present invention relates to a gasket for a pre-filled syringe, which has a sliding side surface that is coated with an inactive resin film and further cut to form a cut. The cut region is preferably between ring-shaped ribs on the sliding side surface, or in a ring-shaped rib on the sliding side surface.

3 Claims, 3 Drawing Sheets

GASKET FOR PRE-FILLED SYRINGE

TECHNICAL FIELD

The present invention relates to a gasket for a pre-filled syringe.

BACKGROUND ART

Nowadays, pre-filled syringes in which a chemical liquid is filled in advance are increasingly used because of their greater convenience of use and prevention of misuse. The rubber members of such a pre-filled syringe are directly in contact with a chemical liquid until the syringe is used. Therefore, often used are butyl rubber-based gaskets and nozzle caps which have excellent chemical resistance, gas permeation resistance, water vapor permeation resistance, and aging resistance.

When a butyl rubber member is used as a gasket or a nozzle cap, the inner wall surface of the syringe and the rubber surface of the gasket or nozzle cap are coated with an oil-type or curable silicone as a lubricant in order to improve sliding properties of the gasket or prevent firm fixing of the nozzle cap. However, the quality of some kinds of preparations may be seriously adversely affected by the silicone coating agent fallen off the barrel inner wall or rubber member as a foreign substance. Also, some bio-preparations are susceptible to interaction with substances eluted from the rubber materials. In order to solve these problems, silicone-free glass or resin pre-filled syringes have been developed by laminating a fluororesin film or the like onto a rubber.

However, the use of a polytetrafluoroethylene (PTFE) film which has a low friction coefficient does not always provide sufficient sliding properties. A known method for achieving both sealing performance and low sliding resistance is to set the compression ratio and contact area within specific ranges (Patent Literature 1). However, the method is not always sufficiently effective. Another known method is a method in which a plurality of annular ridges are formed continuously and integrally at a front portion of a gasket to satisfy both sealing performance and low sliding resistance (Patent Literature 2). However, the method has difficulty in forming thin annular ridges on a mold.

CITATION LIST

Patent Literature

Patent Literature 1: JP S57-22766 A
Patent Literature 2: JP 2006-181027 A

SUMMARY OF INVENTION

Technical Problem

The present invention aims to provide a pre-filled syringe coated with a resin film, which enables to reduce sliding resistance and prevent liquid leakage by a simple method.

Solution to Problem

The present inventors have found that cutting of a part of a resin film coated on a pre-filled syringe releases stress and improves sliding resistance, leading to completion of the present invention. Specifically, the present invention relates to a gasket for a pre-filled syringe, having a sliding side surface that is coated with an inactive resin film and further cut to form a cut.

The cut region is preferably between ring-shaped ribs on the sliding side surface, or in a ring-shaped rib on the sliding side surface.

The inactive resin film is preferably made of polytetrafluoroethylene, a tetrafluoroethylene-ethylene copolymer, a modified derivative of the polytetrafluoroethylene or tetrafluoroethylene-ethylene copolymer, or ultra-high-molecular-weight polyethylene.

The inactive resin film preferably has a thickness of 20 to 150 μm.

Advantageous Effects of Invention

The gasket provided according to the present invention has a sliding side surface that is coated with an inactive resin film and further cut to form a cut. Therefore, the gasket reduces sliding resistance and does not cause liquid leakage from a pre-filled syringe despite of the low sliding resistance.

DESCRIPTION OF EMBODIMENTS

The gasket for a pre-filled syringe of the present invention characteristically has a sliding side surface that is coated with an inactive resin film and further cut to form a cut. FIGS. 1 to 5 show partial cross-sectional views of gaskets for pre-filled syringes of the present invention.

When a gasket is prepared by integrating a resin film made of polytetrafluoroethylene or the like with a Young's modulus of 0.5 GPa and rubber with a Young's modulus of about 0.01-0.1 GPa, i.e. materials having greatly different Young's modulus values, the resin film on the surface of the gasket is stretched and stress remains. If such a gasket is compressed into a syringe, the stress cannot be released and thus strain is applied in the gasket. As a result, sliding resistance tends to increase. According to the present invention, performing cutting on the film makes it possible to release the stress to reduce strain to thereby allow the gasket to slide smoothly.

Figure 1:
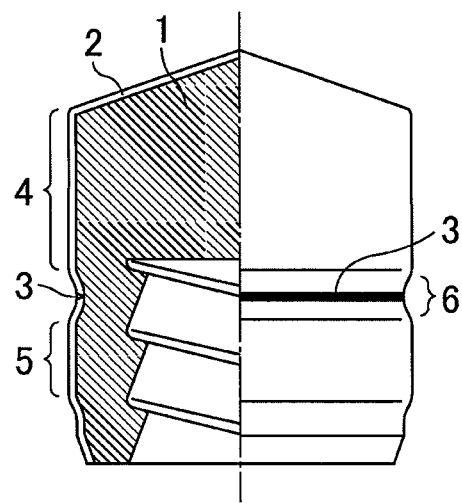
FIG. 1 is a partial cross-sectional view of gaskets for a pre-filled syringe of the present invention prepared in Examples 1 to 3.
Figure 2:
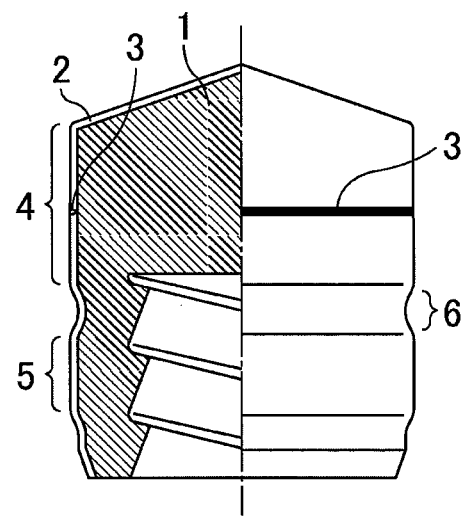
FIG. 2 is a partial cross-sectional view of a gasket for a pre-filled syringe of the present invention prepared in Example 4.

The cut region is on the sliding side surface coated with an inactive resin film. Cutting may be performed on a portion that is or is not to be in sliding contact with a side surface of a barrel as long as the portion is on the sliding side surface. For example, the cut may be formed not only in a valley portion between a front ring-shaped rib forming portion and a back-end ring-shaped rib forming portion (a portion that is not to be in sliding contact with a side surface of a barrel) as shown in FIGS. 1, 3, 4, and 5, but also in a front ring-shaped rib forming portion or a back-end ring-shaped rib forming portion (a portion that is to be in sliding contact with a side surface of a barrel) as shown in FIG. 2.

Figure 6:
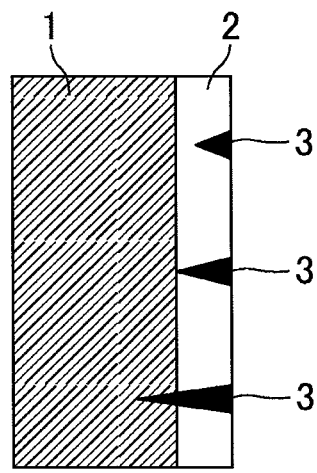
FIG. 6 is a conceptual view showing embodiments of cutting.
Figure 7:
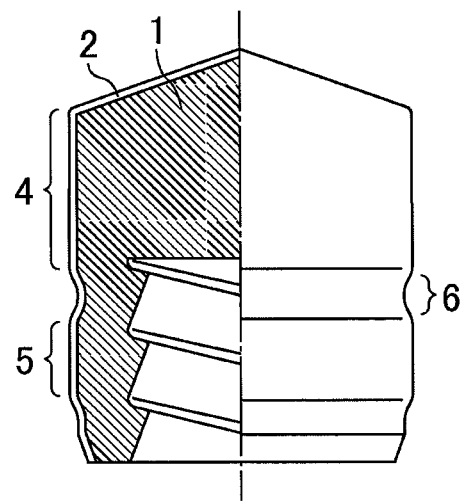
FIG. 7 is a partial cross-sectional view of a conventional gasket for a pre-filled syringe prepared in Comparative Example 1.

The cutting depth is not particularly limited. As shown in FIG. 6, for example, cutting may be performed only on the inactive film (the top embodiment), or to the same depth as the thickness of the inactive film (the middle embodiment), or until the cut reaches the rubber portion through the inactive film (the bottom embodiment). In particular, cutting is preferably performed until the cut reaches the rubber portion through the inactive film, in terms of increasing processability and reducing sliding resistance.

Figure 3:
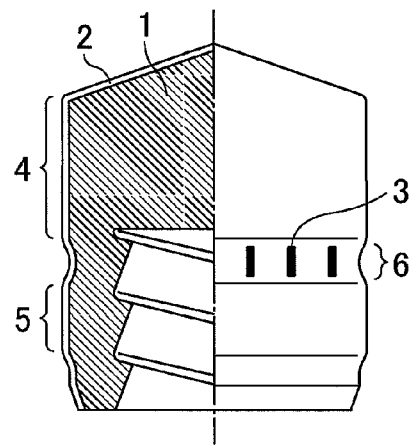
FIG. 3 is a partial cross-sectional view of a gasket for a pre-filled syringe of the present invention prepared in Example 5.
Figure 4:
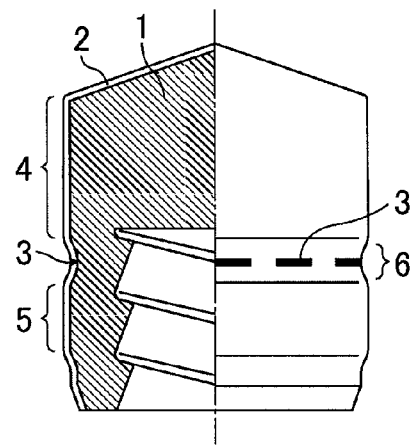
FIG. 4 is a partial cross-sectional view of a gasket for a pre-filled syringe of the present invention prepared in Example 6.
Figure 5:
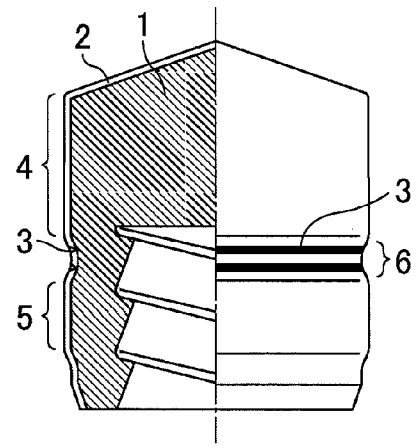
FIG. 5 is a partial cross-sectional view of a gasket for a pre-filled syringe of the present invention prepared in Example 7.

The cutting form is not particularly limited. Examples thereof include a ring-shaped cut formed circumferentially and continuously as shown in FIGS. 1 and 2; two or more ring-shaped cuts formed circumferentially and continuously as shown in FIG. 5; and a series of cuts formed discontinuously (intermittently) as shown in FIGS. 3 and 4. In particular, two or more ring-shaped cuts formed circumferentially and continuously are preferred in terms of increasing processability and reducing sliding resistance.

The method of cutting is not particularly limited and examples thereof include slitter cutting using an ordinary blade, heat cutting using heat, and laser cutting using a laser ($CO_2$ laser/YAG laser). Slitter cutting which is a physical method using a blade enables to provide a smooth slit surface. Heat cutting in which a material is slit while being melted with heat enables to reduce fraying to prevent formation of foreign substances, which keeps a clean environment. Laser cutting in which cutting patterns can be selected enables to provide complex patterns of slits. Also usable are punching methods including physical punching using a needle and laser punching. Needle punching is a simple method, whereas laser punching is complicated but enables to form complex patterns. Particularly preferred are physical methods using a blade or a needle because they can cut materials without heat deterioration and heat discoloration.

The inactive resin film preferably has a thickness of 20 to 150 μm, more preferably 50 to 100 μm. A thickness of less than 20 pm tends to increase breakage of the film during molding. A thickness exceeding 150 μm tends to cause poor dimensional stability of the molded product, higher cost, and poor economical efficiency.

The resin forming the inactive resin film is not particularly limited, and is preferably at least one fluororesin selected from the group consisting of tetrafluoroethylene-ethylene copolymers (ETFE), polytetrafluoroethylene (PTFE), and polychlorotetrafluoroethylene (PCTFE), and/or an olefinic resin in order to obtain good chemical resistance. Meanwhile, medical containers may be sterilized by steam sterilization, ethylene oxide gas sterilization, or gamma ray sterilization. PTFE is less resistant to gamma rays. Therefore, ETFE, modified ETFE, and PCTFE are particularly preferred owing to their high resistance to gamma ray sterilization.

Here, ETFE refers to a copolymer of ethylene and tetrafluoroethylene at a molar ratio of 30/70 to 70/30. The ETFE may be further copolymerized with another component for modification to form a modified ETFE. Examples of the other component include fluorine-containing olefins and hydrocarbon olefins. Specific examples thereof include a-olefins such as propylene and butene; fluorine-containing olefins such as hexafluoropropylene, vinylidene fluoride, perfluorobutyl ethylene, and trifluorochloroethylene; vinyl ethers such as ethylene vinyl ether, perfluorometyl vinyl ether, and perfluoropropyl vinyl ether; and fluorine-containing acrylates. They are copolymerized in an amount of about 2-10 mol % to modify ETFE.

The modified ETFE used may suitably be an ETFE containing a functional group which imparts adhesion. Examples of the functional group include a carboxyl group, an anhydrous carboxyl group, an epoxy group, a hydroxyl group, an isocyanate group, an ester group, an amide group, an aldehyde group, an amino group, a cyano group, a carbon-to-carbon double bond, a sulfonate group, and an ether group. Commercial products of the modified ETFE include Fluon AH-2000 produced by Asahi Glass Co., Ltd.

Examples of olefinic resins include polyethylenic resins such as polyethylene, ethylene-propylene copolymers, ethylene-propylene-nonconjugated diene copolymers, ethylene-butene copolymers, ethylene-hexene copolymers, ethylene-octene copolymers, ethylene-vinyl acetate copolymers, ethylene-vinyl alcohol copolymers, ethylene-ethyl acrylate copolymers, and chlorinated polyethylene; polypropylenic resins such as polypropylene, propylene-ethylene random copolymers, propylene-ethylene block copolymers, and chlorinated polypropylene; polybutene; polyisobutylene; polymethylpentene; and copolymers of cyclic olefins. Preferred is polyethylene (especially, ultra-high-molecular-weight polyethylene (UHMWPE)). These olefinic resins may contain fluorine.

The inactive film is preferably subjected to a treatment for enhancing adhesion to rubber or the like. Examples of such a treatment for enhancing adhesion include chemical treatments, treatments of roughing the surface of a film, and combinations thereof. Specific examples thereof include sodium treatment, glow discharge treatment, plasma treatment (discharge treatment) under atmospheric pressure or in vacuum, excimer laser treatment (discharge treatment), and ion beam treatment.

The gasket base material may be any elastic material. Examples of the elastic material include various rubber materials such as natural rubber, butyl rubber, isoprene rubber, butadiene rubber, styrene-butadiene rubber, silicone rubber, epichlorohydrin rubber, ethylene-propylene rubber, and nitrile rubber; and various thermoplastic elastomers such as polyurethane elastomers, polyester elastomers, polyamide elastomers, olefinic elastomers, and styrenic elastomers. These elastic materials may be used alone or two or more of these may be blended before use. Particularly preferred are materials which acquire elasticity by vulcanization. In the case of vulcanizable materials, compounding agents known in the rubber industry, such as vulcanizing agents (e.g. sulfur) and vulcanization accelerators, may be appropriately added.

The JIS A hardness of the gasket base material is not particularly limited. It is preferably 50 to 70 degrees, and more preferably 55 to 65 degrees. A JIS A hardness of lower than 50 degrees may cause leakage due to deformation of the gasket during sliding or cause removal of a plunger rod from the gasket during suction. Conversely, a JIS A hardness of higher than 70 degrees may require a higher molding pressure, which tends to cause the film to break easily and make it difficult to demold the gasket.

The compression set of the gasket base material is also not particularly limited. It is preferably 20% or lower, and more preferably 15% or lower. A compression set of higher than 20% tends to cause diameter reduction of the ring-shaped rib during plugging, sterilization, and storage so that the compression ratio becomes insufficient, thereby failing to maintain the liquidtightness and airtightness between the ring-shaped rib and a barrel inner wall. The compression set herein means the value measured after 22 hours at 70±1° C. and 25% compression.

The gasket of the present invention can be obtained as follows. The compounding materials are kneaded at a predetermined compounding ratio using an internal mixer, an open roll mill or the like to prepare a kneaded mixture. This kneaded mixture is formed into an unvulcanized rubber sheet using a calender or sheet forming machine. Then, the unvulcanized rubber sheet with a predetermined weight and size and an inactive film are stacked and put on a mold, and then molded using a vacuum press. This yields a molded sheet of laminated gaskets.

The molding conditions are not particularly limited and may be appropriately determined. The molding temperature is preferably 155° C. to 200° C., and more preferably 165° C. to 180° C. The molding time is preferably 1 to 20 minutes, more preferably 3 to 15 minutes, and still more preferably 5 to 10 minutes.

EXAMPLES

The present invention will be described in detail hereinafter referring to, but not limited to, examples.

Laminating film: modified PTFE skived film, trade name "NEW VALFLON" (film thickness: 70 μm, one surface was adhesive-treated) produced by NIPPON VALQUA INDUSTRIES, LTD.

Gasket base material: Chlorinated butyl rubber (JIS A hardness: 60 degrees)

Examples 1 to 7 and Comparative Example 1

An unvulcanized rubber sheet made of chlorinated butyl rubber and a PTFE film were stacked and put on a mold, and then molded and vulcanization-bonded by a vacuum press at 175° C. for 10 minutes. Cutting of the resulting gaskets was performed in different manners to prepare gaskets of Comparative example 1 and Examples 1 to 7. The cutting was performed by slitter cutting, that is, by contacting a blade with the gasket at an appropriate depth and rotating the gasket. Or, longitudinal cutting was performed by pressing a blade having an appropriate length onto the gasket. The cutting depths shown in Table 1 are as follows:

"half-cutting" refers to cutting to a depth of half the thickness of the resin film; "film only" refers to cutting to the same depth as the thickness of the resin film; and "rubber portion" refers to cutting into the rubber portion to a depth of 0.5 mm. The cutting form in each example is as follows: a slit was formed (continuously) along the whole circumference of the valley portion in Examples 1 to 3 (FIG. 1); a slit was formed along the whole circumference of the front ring-shaped rib portion in Example 4 (FIG. 2); longitudinal slits were formed in the valley portion in Example 5 (FIG. 3); intermittent (discontinuous) slits were formed along the whole circumference of the valley portion in Example 6 (FIG. 4); and two or more slits were formed along the whole circumference of the valley portion in Example 7 (FIG. 5).

(Sliding Resistance Value)

A jig with a certain length was fit into the screw portion of the gasket, and the gasket in this state was placed with the liquid-contact side facing up. Then, the gasket was inserted straight into a syringe barrel so that the syringe was plugged. Then, a liquid was ejected at a speed of 100 mm/min with an autograph until the gasket reached a position 10% of the maximum capacity. During this movement, the average value was determined. The measurement was performed with n=10, and the sliding resistance was evaluated based on the following criteria. Table 1 shows the results.

Syringe capacity: 1 ml, syringe inner diameter: 6.35 mm, syringe material: COP (resin)

Good: Smoothly move at 10 N or lower without knocking
Acceptable: Move at 12 N or lower
Poor: Move at 12 or higher (Liquid Leakage)

This test was performed in conformity with the Notification "Mekkin-zumi chusha-tou kijun (standards for sterile injection syringes)" issued on Dec. 11, 1998, Iyakuhatsu No. 1079 by the Director of the Pharmaceutical and Medical Safety Bureau, the Ministry of Health, Labour and Welfare.

A jig longer than the screw was fit into the screw portion of the gasket, and the gasket in this state was placed with the liquid-contact side facing up. Then the gasket was inserted straight into a syringe barrel so that the syringe was plugged. Next, water colored by methylene blue was charged through the nozzle into the syringe to a graduation line corresponding to ¾ of the nominal capacity. Then, the nozzle cap and the plunger were attached. The syringe was faced down and a predetermined pressure (1-ml syringe: 490 kPa) was applied to the plunger for 10 seconds. After the syringe was left to stand for one day, the syringe was observed at a magnification of 10× for the presence of leakage into the valley portion (between the front ring-shaped rib and the back-end ring-shaped rib) of the gasket. The evaluation was carried out with n=20 based on the following criteria. Table 1 shows the results.

Syringe capacity: 1 ml, syringe inner diameter: 6.35 mm, syringe material: COP (resin)

Good: No leakage was observed.
Acceptable: Slight linear leakage was observed.
Poor: Leakage was clearly observed.

TABLE 1

| | | Example No. | | | |
| --- | --- | --- | --- | --- | --- |
| | | Comparative Example 1 | Example 1 | Example 2 | Example 3 |
| Cutting form | Cutting position | — | Valley portion | Valley portion | Valley portion |
| | Cutting direction | — | Circumferential direction | Circumferential direction | Circumferential direction |
| | Cutting length | — | Continuous | Continuous | Continuous |
| | Cutting depth | — | Rubber portion | Half-cutting | Film only |
| Evaluation results | Sliding resistance (N) | Acceptable 11.8 | Good 8.5 | Acceptable 11.5 | Acceptable 10.2 |

TABLE 1-continued

|  |  |  | | | |
|---|---|---|---|---|---|
| Liquid leakage | Good | 20/20 | 20/20 | 20/20 | 20/20 |
|  | Acceptable | 0/20 | 0/20 | 0/20 | 0/20 |
|  | Poor | 0/20 | 0/20 | 0/20 | 0/20 |

|  |  | Example No. | | | |
|---|---|---|---|---|---|
|  |  | Example 4 | Example 5 | Example 6 | Example 7 |
| Cutting form | Cutting position | Front ring-shaped rib | Valley portion | Valley portion | Valley portion |
|  | Cutting direction | Circumferential direction | Longitudinal direction | Circumferential direction | Circumferential direction |
|  | Cutting length | Continuous | Discontinuous | Discontinuous | Continuous |
|  | Cutting depth | Rubber portion | Rubber portion | Rubber portion | Rubber portion |
| Evaluation results | Sliding resistance (N) | 8.7 | 8.1 | 8.9 | 7.9 |
|  | Liquid leakage Good | 20/20 | 20/20 | 20/20 | 20/20 |
|  | Acceptable | 0/20 | 0/20 | 0/20 | 0/20 |
|  | Poor | 0/20 | 0/20 | 0/20 | 0/20 |

As shown by the results of Examples 1 to 7, cutting in the front ring-shaped rib, the valley portion, or the back-end ring-shaped rib relieved strain during sliding and reduced the sliding resistance by 20% to 30% as compared to Comparative Example 1 in which cutting was not performed. In particular, forming two or more cuts in the valley portion was most effective to reduce the sliding resistance. With respect to the cutting depth, cutting into the rubber portion was most effective. On the other hand, a cutting depth exceeding 0.5 mm reduced the circumferential rubber thickness and thus reduced rubber strength, which tended to cause the rubber to break easily. Moreover, since the design of the front ring-shaped rib and back-end ring-shaped rib was unchanged, no harmful influence on airtightness was observed.

REFERENCE SIGNS LIST

1: rubber
2: inactive resin film
3: cut portion (cut)
4: front ring-shaped rib forming portion
5: back-end ring-shaped rib forming portion
6: valley portion

The invention claimed is:

1. A gasket for a pre-filled syringe, comprising:
   a sliding side surface comprising a rubber portion that is coated with an inactive resin film,
   wherein the sliding side surface has a slit, which is formed by cutting a part of the inactive resin film,
   the slit is present from a surface of the inactive resin film to a portion of the rubber portion, and
   the slit is placed at least on a valley portion between ring-shaped ribs on the sliding side surface.

2. The gasket for a pre-filled syringe according to claim 1, wherein the inactive resin film is made of polytetrafluoroethylene, a tetrafluoroethylene-ethylene copolymer, a modified derivative of the polytetrafluoroethylene or tetrafluoroethylene-ethylene copolymer, or ultra-high-molecular-weight polyethylene.

3. The gasket for a pre-filled syringe according to claim 1, wherein the inactive resin film has a thickness of 20 to 150 μm.

* * * * *